(12) United States Patent
Lerche et al.

(10) Patent No.: US 9,019,493 B2
(45) Date of Patent: Apr. 28, 2015

(54) METHOD AND DEVICE FOR THE CHARACTERIZATION OF MULTIPLE SAMPLES OF ONE OR VARIOUS DISPERSIONS

(75) Inventors: Dietmar Lerche, Berlin (DE); Titus Sobisch, Berlin (DE); Torsten Detloff, Güstrow (DE); Frank Babick, Dresden (DE); Michael Stintz, Dresden (DE)

(73) Assignee: L.U.M. GmbH, Berlin (DE)

( * ) Notice: Subject to any disclaimer, the term of this patent is extended or adjusted under 35 U.S.C. 154(b) by 0 days.

(21) Appl. No.: 13/565,072

(22) Filed: Aug. 2, 2012

(65) Prior Publication Data

US 2012/0293799 A1    Nov. 22, 2012

Related U.S. Application Data

(63) Continuation of application No. 10/591,701, filed as application No. PCT/EP2005/050988 on Mar. 4, 2005, now Pat. No. 8,265,882.

(30) Foreign Application Priority Data

Mar. 5, 2004  (DE) .......................... 10 2004 011 387

(51) Int. Cl.
*G01J 3/28* (2006.01)
*G01N 15/02* (2006.01)
*G01N 15/04* (2006.01)

(52) U.S. Cl.
CPC .......... *G01N 15/0205* (2013.01); *G01N 15/042* (2013.01)

(58) Field of Classification Search
CPC .......... G01N 15/042; G01N 2015/045; G01N 27/44721; G01N 15/0205

USPC ............................................. 356/326; 494/10
See application file for complete search history.

(56) References Cited

U.S. PATENT DOCUMENTS

| 3,344,702 A | 10/1967 | Wood et al. | |
|---|---|---|---|
| 3,928,140 A * | 12/1975 | Wyatt et al. | ..................... 435/32 |

(Continued)

FOREIGN PATENT DOCUMENTS

| EP | 0 823 633 A | 2/1998 |
|---|---|---|
| WO | WO 97/16713 A2 | 5/1997 |

OTHER PUBLICATIONS

Fieberg et al., "UV curable electrodeposition systems", 2002, Elsevier, Progress in Organic Coatings, vol. 45, pp. 239-247.*

(Continued)

*Primary Examiner* — Kara E Geisel
(74) *Attorney, Agent, or Firm* — Buchanan Ingersoll & Rooney PC (57) ABSTRACT

A method and a device for the automatic determination of selected physical and colloidal chemistry parameters by determining the attenuation of radiated waves through monodisperse or polydisperse dispersion samples subjected to gravitation or centrifugation, wherein during the segregation by means of centrifugation or gravitation, the instantaneous transmission $I_T(t, r)$ characterizing the current segregation status of the waves radiated with the intensity $I_o(t, r)$ and/or the instantaneous scattering $I_S(t, r)$ as a function of the position within the samples is repeatedly determined and recorded at high resolution at any arbitrary time for one or more wavelengths over the entire length of the sample or in selected partial sections of it, simultaneously for multiple and even concentrated samples with known and/or unknown physical and colloidal chemistry properties.

18 Claims, 8 Drawing Sheets

(56) References Cited

U.S. PATENT DOCUMENTS

| | | | |
|---|---|---|---|
| 3,932,131 A | | 1/1976 | Rolfo-Fontana |
| 3,997,845 A | | 12/1976 | Wegstedt |
| 4,311,394 A | * | 1/1982 | Manabe ................ 356/440 |
| 4,975,578 A | | 12/1990 | Tomimasu et al. |
| 5,095,451 A | | 3/1992 | Allen |
| 5,279,150 A | * | 1/1994 | Katzer et al. ............ 356/246 |
| 5,309,216 A | * | 5/1994 | Weichert ................. 356/442 |
| 5,638,172 A | | 6/1997 | Alsmeyer et al. |
| 5,888,184 A | * | 3/1999 | Wardlaw ................. 494/37 |
| 6,336,358 B1 | * | 1/2002 | Kishimori et al. ........ 73/61.69 |
| 2002/0147563 A1 | | 10/2002 | Lerche et al. |
| 2002/0167662 A1 | * | 11/2002 | Tanaami et al. ............ 356/318 |
| 2005/0025819 A1 | | 2/2005 | Onyuksel et al. |
| 2005/0275837 A1 | | 12/2005 | Zhang et al. |

OTHER PUBLICATIONS

International Search Report (Form PCT/ISA/210) dated Jul. 1, 2005, issued in PCT/EP2005/05098.

Lerche, D., "Process and Device for Determining Rheological and Mechanical Characteristics of Materials," May 9, 1997, pp. 1-34, English translation of WO 97/16713 A2.

PS Prozesstechnik GmbH, http://www.prozesstechnik.com, pp. 1-3, Oct. 6, 2011 (originally indicated by the Patent Office as "no date").

\* cited by examiner

Figure 5 during the segregation, repeatedly determining and recording momentary transmission values $I_T(t,r)$, and optionally scattering values $I_S(t, r)$, characterizing a current segregation status of the sample using waves radiated with intensity values $I_0(t, r)$ as a function of a position r within the sample at a time t, for one or more wavelengths over at least a partial section of the sample, simultaneously for multiple positions r, wherein the repeated determination of momentary transmission values $I_T(t, r)$, and optionally scattering values $I_S(t, r)$, is conducted with the measurement device calculating extinction profiles $E_T(t, r)$ by finding a log of a ratio of $I_0(t, r) / I_T(t, r)$ for a determination of a particle or droplet concentration for the dispersion sample as a function of the sample position and time from the extinction profiles $E_T(t, r)$ determined at different times and a local adjustment made in time segments, calculating segregation speeds for any constant extinction values from a ratio of the segregation speeds determined for specific extinction percentiles, calculating a polydispersity index

FIG. 6 radiating the sample with waves having intensity values $I_0(t, r)$, at multiple positions r of the sample at a time t during segregation of the sample, detecting transmission values $I_T(t, r)$ and/or scattering values $I_S(t, r)$ of the sample, simultaneously for multiple positions r, characterizing a segregation status of the sample from the transmission values $I_T(t, r)$ and/or scattering values $I_S(t, r)$

METHOD AND DEVICE FOR THE CHARACTERIZATION OF MULTIPLE SAMPLES OF ONE OR VARIOUS DISPERSIONS

CROSS REFERENCE TO RELATED APPLICATIONS

This application is a continuation of application Ser. No. 10/591,701, filed Jul. 9, 2007, which was the National Stage filing under §371 of PCT/EP2005/050988, filed Mar. 4, 2005, which in turn claims priority to German Application No. 10 2004 011 387.4 filed Mar. 5, 2004. The contents of each of the above applications are herein incorporated by reference.

BACKGROUND

The characterization of fluid-fluid or fluid-solid dispersions, for example with respect to segregational stability and structural stability, as well as the separation behavior in the centrifugal field, is an important task in research, the design of (large) technical separation processes, the development of new products, as well as in quality control close to the production line. The particle size, as well as the distribution of particle sizes, plays a special role here. Ideally, this is to be surveyed without dilution, which means in the original state, because changing the composition can also lead to changes in the measured size (dilution agglomeration, for example).

There are a number of different measurement methods known, which are distinguished with respect to the physical measurement procedure, the area of application (for example, concentration of the sample, range of particle sizes) as well as the measurement options (for example, resolution, type of particle size distribution, measurement accuracy) (Allan, T.: Particle Size Measurement, Kluwer Academic Publishers, Netherlands (1999)/Leschonski, K.: Particle measurement technology, report from the Bunsen Company for Physical Chemistry, (1984)). Regardless of whether fractionated or non-fractionated measurement techniques are involved, all instruments used up until now allow the determination of the particle size of only one sample. In other words, multiple samples must always be measured one after the other. First, this is costly in terms of time because the samples to be measured are often away from the measurement chamber, the chamber must be washed and dried, and the next sample must be poured in. Second, the samples are not measured under identical conditions (for example, temperature drift, subjective and hardware-caused settings particularities, erroneous settings, electronic noise level). Third, a validation of the instruments and/or the measurement for a reference sample is not possible in parallel, which means simultaneously with the actual measurement. In addition, common to all known methods is that various substance parameters (for example, viscosity of the dispersion medium, optical constants) for the samples to be analyzed must be known even for diluted samples, in order to be able to calculate a distribution of particle sizes from the measurement results evaluated based on volume. For concentrated dispersions, additional particle-particle interaction effects and particle-fluid interaction effects are to be taken into consideration, such as the increasing substance-specific hydrodynamic interaction (hindrance function) that is non-linear with the volume concentration, for example. This substance characteristic is of importance for high-resolution fractionated measurement methods in particular.

Until now, the sample-specific data had to be compiled through previous tests of the sample both with rheologic and optical measurement methods, and prepared in a suitable manner, for example using special input menus for the respective analysis procedures for the determination of particle sizes. The entire procedural chain is very costly in terms of time, is tainted by measurement errors and cannot be automated. It also proves to be particularly limiting that the predominant majority of the particle size measurement methods can only be used for diluted or even highly-diluted substance samples. For this reason, many micro-dispersions and nano-dispersions cannot be measured under conditions that are close to the product.

Although fractionated measurement methods are distinguished from non-fractionated methods (for example, static or dynamic light scattering) by a significantly higher resolution, in particular for polymodal samples, the previous technical solutions realized are characterized by a series of inadequacies. The following fractionated measurement methods are currently known for dispersions: Gravity sedimentation methods, centrifugal field sedimentation methods (disc centrifuges, photo cuvette centrifuges and manometer centrifuges)

Disc centrifuges are laboratory devices with a sample chamber in the form of a disc, which is accelerated to between 600 and 24,000 revolutions per minute$^{-1}$ (CPS Instruments, Inc. USA, http://www.cpsinstruments.com/Brookhaven Instruments Corporation USA, http://www.bic.com). When the specified final speed is reached, the suspension to be analyzed is introduced onto the surface of a fluid that was poured into the sample chamber in advance. In principle, the sample is quite heavily diluted by doing so. In addition, hydrodynamic instabilities often occur when "immersing" the particles into the spinning fluid. This leads to starting times and starting speeds that are tainted with errors. Since the temperature of the measurement chambers cannot be maintained, a calibration measurement for determining the current base value must first be established by means of reference particles for the density and viscosity of the spinning fluid, which are dependent on the temperature. In principle, this involves the risk of impurity from the displacement of reference particles into the sample to be subsequently applied.

As a result of the centrifugal force, the particles begin to migrate outwards according to their size. A suitable source of radiation is positioned such that radiation is transmitted through the disc at a position determined by the manufacturer, for the most part at the outside edge. Through scattering and absorption, the sedimenting particles reduce the intensity of the radiation, which is measured by a sensor at a constant position. From the time elapsed and the particle migration and the measurement of the attenuated radiation intensity, the size and the concentration of the particles are determined. Disc centrifuges are in the position to detect particles in the range of sizes from 0.01 μm to 40 μm. The sample throughput is limited by the fact that only one sample can be measured in each case.

Known photo cuvette centrifuges likewise measure the opacity of a light beam or laser beam only for one sample and at one level (Shimadzu Scientific Instruments (SSI) North America: http://www.ssi.shimadzu.com/Horiba: http://www.horiba-particle.com/). In contrast to the disc centrifuges, the particles are evenly dispersed in a transparent cuvette at the start of the test. As a result of the centrifugal acceleration, the particles begin to settle and pass the light sensor according to individual size classes. For this reason, the opacity decreases with time, and the particle size distribution can be calculated from this temporal transmission increase and the associated sedimentation velocity.

A measurement of the particle concentration by means of a detection method for electromagnetic radiation forms the basis of both methods, the disc centrifuge and the photo cuvette centrifuge. Corresponding to the prior art, radiation sources are used in the visible range for the determination of the particle size distribution. The extinction coefficients that depend on particle size corresponding to the Mie Theory are required for a calculation of the particle size distribution evaluated on the basis of volume or mass (van de Hulst, H. C.: Light Scattering by Small Particles, Dover Publications Inc., New York (1981)/Kerker, Milton: The scattering of light and other electromagnetic radiation, Academic Press, New York, San Francisco, London, (1967)).

If X-ray radiation is used, absorption coefficients that depend on particle size can be used. However, in addition to the technical radiation safety aspects, this has the disadvantage that only samples with materials of higher atomic numbers (typically >13) can be measured. Biological samples, for example, cannot be analyzed for this reason.

In order to test the sedimentation behavior that is dependent on particle sizes for particles in the centrifugal field, a manometer centrifuge can be used, whose principle is based on the measurement of the hydrodynamic difference in pressure between two measurement levels in a sedimentation cell (Beiser, M., Stahl, W.: Influence of Additives on the Sedimentation Behaviour of Fine Grained Solids in the Centrifugal Field, Filtech Europe 2003—Conference Proceedings, Volume I-L-Session, page I-465-I-472). When a solid substance that has a higher density than the fluid precipitates out, the average mass density of the suspension volume between the two measurement levels decreases continuously, and the hydrodynamic difference in pressure likewise reduces as a result. The process continues until the separation level between the clear liquid and the sedimentation zone has passed the lower measurement level. If all particles settle at the same speed, the difference in hydrodynamic pressure decreases linearly with time. However, if there are particles in the suspension that settle rapidly and slowly, the change in pressure is initially made up of both parts, and if the particles settling more rapidly have left the measurement volume, the slope of the pressure curve changes. If n particle classes are present in the suspension, n−1 inflexion points result in the temporal pressure curve, or a non-linear curve for a continuous particle size distribution. Information about the sedimentation mechanisms can be derived from these pressure curves, i.e. at what concentrations the transition between zone and cluster sedimentation lies, for example. A large disadvantage is the costly measurement of the pressure in the rotating sedimentation cell and the output of the temporal pressure curve during the centrifugation. Even here, only one sample can be tested during a measurement.

In addition, it is common for the technical devices for the previously described centrifugation method to be targeted to the measurement of suspensions. If anything, a modification must be made for the measurement of emulsions. Mixed dispersions (milk products, for example) that exhibit simultaneous flotation and sedimentation segregation in principle could not be analyzed with this method with respect to particle size without prior separation.

In the European patent specification EP 0 840 887 B1, a method and a device for the automatic analysis of geometric, mechanical and rheological parameters of substance systems and materials is described, which is based on the different cuvettes or measurement systems matched to the tested commodity and the test parameter(s), which are also placed in different positions radially, being placed on a carriage or rotor positioned horizontally or vertically, and being subjected to a time-variable acceleration that is preset or controlled depending on the course of the process. The change in the local and temporal composition of the substance system induced by the acceleration, the geometric arrangement or position of the materials, or the position of the corresponding sample specimen is detected with high resolution by means of mechanical or electromagnetic waves. Multiple material characteristics—such as sedimentation velocity, flotation velocity, viscosity, viscoelasticity, concentration by volume, distribution of particle sizes, particle types, elasticity, adhesion, adhesiveness or tensile strength—as well as their time dependencies are calculated online or offline simultaneously from these signals using appropriate algorithms.

The subject matter of the patent applications DE 102 08 707.5-52 A1 and EP 1 386 135 A2 is a method and a device, with which both the stability or instability of a dispersion can be measured, or with which stabilizing or destabilizing effects on a dispersion can be tested. At the same time, the instantaneous measurement of the local composition of the dispersion is made possible with high local and temporal resolution using the overall level of the measurement cells as well as their temporal change in intervals of a hundredth of a second without movement of measurement cell, transmitter or receiver in relation to one another.

Likewise, for the multi-channel devices from the patent specifications EP 0840887 B1, DE 102 08 707.5-52 A1 and EP 1 386 135 A2, the transmission is recorded, solved in terms of location and time without a temperature option (exception patent specifications DE 102 08 707.5-52 A1 and EP 1 386 135 A2) for the samples. Until now, it has proven particularly disadvantageous here that the transmission signal was recorded only as a virtual, device-dependent intensity, and that the method extended primarily to the ascertainment of the particle-free solution/dispersion boundary layer. A conversion of the transmitted intensity into extinction values proportional to concentration was not provided either for dilute or for undiluted dispersions in particular. Also lacking are appropriate mathematical algorithms that make possible the simultaneous experimental determination of the particle sizes of a sample and the substance-specific characteristics (for example, size-related extinction coefficients, hindrance or flux density function that depend on concentration) required for the calculation of these sizes using the multi-channel capability under the same measurement conditions and with the same measurement values. An automatic software-based analysis and documentation of these characteristics was not provided.

An object of the invention is based on the elimination of the disadvantages of the solutions described in the prior art.

SUMMARY

An object is achieved according to the invention in that, by means of a spectroscopic measurement device functioning in a linear range (light source, condenser, line receiver), the attenuation caused by the particles of the dispersion (for example through absorption and/or scattering) is ascertained with respect to the radiated intensity of waves of one or more wavelengths. The scattered intensity can be detected alternatively or simultaneously. The transmitted and/or scattered intensity is determined, stored and analyzed over the entire extent of the sample, resolved for both location and time. The developed algorithms make possible the analysis according to the invention of the extinction changes at different selectable locations in the measurement sample depending on the time, or as a function of the position within the measurement sample for different selectable times. At the same time, it is particularly advantageous that the corresponding determination of the analysis mode as well as the corresponding locations and times must take place only during the analysis after the experiment, and can be revised with arbitrary frequency, and thus even highly complex dispersions (suspoemulsions, for example) are to be analyzed easily. It has also proven advantageous that, in addition to the samples with unknown particle size distributions to be analyzed, simultaneous reference samples with different volume concentrations and/or known particle size distributions are carried out at the same time, and from the results for the reference samples acquired under identical measurement conditions, the optical parameters indispensable for the determination of the particle size distribution for the unknown samples as well as the hindrance and flux function (function for the description of the transport in terms of the cross section) in the case of concentrated samples can be calculated. Surprisingly, it turned out that the solution according to the invention also made it possible to determine the relative apparent viscosity as a function of the particle concentration as well as substance-specific parameters for rheologic equations.

The equipment for the method according to the invention makes possible the segregation of 12 different samples in the gravitation or centrifugal field, for example, and the detection of the discharged intensity $I_T(t, r)$ over the entire length of the sample by means of a CCD line as a receiver matched to the wavelength (880 nm, for example; others are possible) of the radiation source, for example. The range of observation can be extended by shifting a CCD line or other suitable punctiform sensors gradually along the cuvettes. With respect to the known disc and photo cuvette centrifuges, the discovered solution also makes possible the use of optical path lengths to the cuvettes coordinated to the starting opacity, and the variation of the radiated intensity. The measurement of concentrated samples can also be realized by doing so. The entire spectroscopic measurement device as well as the samples are maintained at a temperature of from 4° C. to 60° C., for example, during the measurement for achieving the required analysis accuracy. It also arose that the method according to the invention is not in the position to analyze floating substance systems like emulsions in terms of selected physical and colloidal chemistry parameters without changes to the measurement apparatus, but surprisingly even mixture systems that contain particles with more limited and greater densities than the suspension medium can be characterized without separation by particle sizes in advance.

The method according to the invention and the device according to the invention make it possible for the first time to automatically determine selected physical and colloidal chemistry parameters (for example, the particle size, the distribution of particle sizes, the hindrance function (function that describes the deviation of the sedimentation behavior from the Stokes law) and indices of structural stability (different characteristics for structural stability, for example flow limits) for dispersion samples through the determination of the spatially and temporally resolved impairment of radiated waves through the monodisperse or polydisperse dispersion samples subject to gravitation or centrifugation (dispersions with uniform or deviating particle sizes). It should be analogously applicable without prior separation for floating (creaming) and sedimenting substance systems, as well as for mixtures of them.

The method according to the invention for the automatic determination of selected physical, technical method and colloidal chemistry parameters (for example, the particle size, the distribution of particle sizes, the speed distribution, the particle flux (particle transport related to cross-section), the hindrance function and indices of structural stability) takes place by means of the determination of the attenuation of radiated waves during the segregation of monodisperse or polydisperse dispersion samples subjected to gravitation or centrifugation, and includes the following steps/partial steps:

During the centrifugation, the instantaneous transmission $I_T(t, r)$ characterising the current segregation status of the waves radiated with the intensity $I_o(t, r)$ is repeatedly determined and recorded at high resolution at any arbitrary time for one or more wavelengths over the entire length of the sample or in selected partial sections of it, simultaneously for multiple and even concentrated samples with known and/or unknown physical and colloidal chemistry properties. Alternatively or at the same time, in addition to the transmission, the instantaneous scattering $I_S(t, r)$ can hereby be determined and recorded as a function of the position within the samples. The characterization of the dispersion samples can also take place without centrifugation.

The extinction profile $E_T(t, r)$ is calculated by finding the log of the ratio of $I_o(t, r)/I_T(t, r)$ as a basis for the determination of the particle or droplet concentration for the tested dispersion samples as a function of sample position and time.

From these extinction profiles $E_T(t, r)$ determined at different times (t1 . . . tn) and the local adjustment made in these time segments (t(n−1)−t(n)), segregation speeds are calculated for any constant extinction values.

From the ratio of the segregation speeds determined for specific extinction percentiles, a polydispersity index (measure of the breadth of the distribution) is calculated, which is characteristic for the polydispersity of the density or the particle or droplet size.

Extinction-weighted distributions of the particle size are calculated from extinction profiles $E_T(t, r)$ for selectable times according to Equation A (see below) while standardising on the maximum extinction for this profile. As a supplement thereto, the local and temporal change of the particle or droplet concentration can be determined, taking into account the substance-specific extinction-concentration relationship.

The determination of the substance-specific extinction-concentration relationship through the simultaneous segregation of samples of the substance system to be measured can be carried out with known, varying volume concentrations, whereby the concentration effect on the extinction is calculated while taking into account the repeated scattering, for example according to Equation B (see below).

From any extinction profiles acquired at time t, the volume-weighted distributions of the particle size are calculated according to Equations A and C (see below). The volume-specific extinction cross section that is dependent on particle size and that is required for doing so (extinction cross section: area on which the same energy falls from the radiation as is masked through absorption and scattering) is calculated according to Mie-theory from the known optical substance parameters and including the device constants. As an alternative to this, the method allows the experimental determination of the volume-specific extinction cross section that is dependent on particle size, if the extinction is determined from at least two monodisperse reference samples.

As an alternative to this, the method allows the experimental determination of the volume-specific extinction cross section that is dependent on particle size, if the course of the extinction is determined during the segregation of at least one polydisperse substance system with similar optical characteristics.

Using the volume-weighted particle or droplet size distribution specified above, the particle size dependency for the volume-specific extinction cross sections determined above, and the concentration-dependent extinction determined, each radial position and the particle size associated with it via Equation A is associated with a concentration by volume corresponding to Equation D (see below).

The flux density function (Equation F—see below) standardised to the centrifugation constant is determined from the change in the concentration of the samples with a known starting concentration. Corresponding to Equations E, E* and F, the concentration-dependent hindrance function for the substance system can be determined.

The volume-weighted distribution of the Stokes equivalent diameter for the case of hindrance functions not equal to 1 is determined by iteratively repeating Equation G instead of Equation A for the steps mentioned above until the differences between the steps following one another for the concentration profiles are less than a value to be provided in advance, or if the allowance for the hydrodynamic impediment (Equation E) is provided by means of another suitable mathematical algorithm, for example via the definition of a cost function.

The determination of the particle sizes and their distribution for dispersed particles is possible with density both greater and less than that of the dispersion medium.

In place of the position-dependent extinction profile $E_T(t, r)$ at time t, the extinction is determined as a function at a freely selectable position or over a range $(r+\delta r)$ of the sample, and the distribution of particle sizes is calculated from it analogously to the above calculation.

The apparent relative viscosity can be calculated as a function of the concentration by volume from the determined hindrance function, taking into account the concentration by volume.

The sedimentation type and the critical concentration by volume for the use of consolidation phenomena can be determined from the change in the segregation speed during the segregation.

The ascertainable range of the particle size distribution as well as the resolution with respect to the distribution of particle sizes can be increased by varying the number of revolutions and the measurement time intervals.

The mass density distribution of the sample is calculated from the extinction profile $E_T(t, r)$ for a known distribution of particle sizes.

For mixtures of substances of different densities, the distribution of particle sizes for the individual substance components is calculated from the extinction profiles for the segregation of dispersions with different densities for the dispersion medium.

For mixtures of substances of different densities, the distribution of particle sizes for the individual substance components is calculated from the extinction profiles for the segregation of dispersions with different densities for the dispersion medium.

Indices for the consolidation behavior of the dispersion samples can be computed from the sediment levels for gradually changed revolutions related to the respective operative centrifugal force.

The control of the segregation analyzer and the measurement sensor, including radiation source, sample management and data transfer, data handling and data storage, as well as all steps of analysis and the documentation of the results, takes place by means of software supported by a database.

The device according to the invention for the automatic determination of selected physical, technical process and colloidal chemistry parameters (for example, the particle size, the distribution of particle sizes, the speed distribution, the particle flux, the hindrance function and of indices of structural stability) consists of a PC-controlled multi-sample receptacle unit arranged vertically or horizontally with a spectrometric measurement device with a source producing monochromatic parallel radiation, which registers, digitises and stores the radiation intensity scattered or transmitted by the respective dispersion sample over the entire length of the sample simultaneously or shifted temporally during the segregation, resolved for location and time.

Different cuvettes matched to the measurement task and/or the dispersion sample with respect to the optical path length and the materials can be used; the cuvette type is detected automatically, and the parameters required for the analysis of the measurement results are automatically made available via database entries for the calculation of the parameters to be analyzed.

Radiation sources of different monochromatic wavelengths, whose radiation intensity $I_o(t, r)$ can be varied, are also used electively in an alternating fashion, depending on the sample and measurement tasks.

The measurement range can be controlled by thermostat, and the measurements can be carried out both above and below room temperature at selectable temperatures.

The multi-sample receptacle unit is designed as a rotor, and is driven by a motor with programmable variable and/or constant revolutions. As an alternative to this, the device according to the invention has a multi-sample receptacle unit, which makes it possible to receive samples placed vertically for segregation in the gravitational field.

The features of the invention develop not only from the claims but from the description as well, whereby the individual features in each case represent advantageous embodiments that are subject to protection, alone or together in the form of combinations, for which protection is applied for with this document. The combination consists of known elements (ascertainment of the attenuation of radiated waves during the segregation of monodisperse or polydisperse dispersion samples subjected to gravitation or centrifugation) and new elements (determination of the parameters through the specified calculation principles), which interact and provide an advantage in their new overall effect (synergistic effect) and the desired result, which is due to the fact that now, for the first time, selected physical and colloidal chemistry parameters (for example, the particle size, the distribution of particle sizes, the hindrance function and indices of structural stability) can be determined automatically for dispersion samples through the ascertainment of the spatially and temporally resolved attenuation of radiation waves through the monodisperse or polydisperse dispersion samples subject to gravitation or centrifugation.

DETAILED DESCRIPTION

The invention is to be explained in greater detail on the basis of exemplary embodiments without being limited to these examples.

Exemplary Embodiment 1

Calculation of the Distribution of Particle Sizes for Known Optical Parameters

From the light intensity from the light source $I_0(t)$, which can be set, and the intensity that is detected by the sensor for a particular position in the sample, a location profile is determined for the transmission $I_T(t, r)$ or the scattering $I_S(t, r)$, and the corresponding extinction profile $E_T(t, r)$ is determined after finding the log of the ratio $I_0(t)$ to $I_T(t, r)$. If the measurement is repeated at different times, it is possible to observe the temporal progress of the sedimentation at the base of the cuvette for a suspended solid substance that has a greater density than the fluid, and to calculate the distribution of particle sizes from that. The following exemplary equations are used to do so (other types of functions are absolutely possible)

$$x(r, t) = \sqrt{\frac{18 \cdot \mu_C}{(\rho_P - \rho_F) \cdot \omega^2 \cdot t} \cdot \ln\left(\frac{r}{r_0}\right)} \quad \text{(Equation A)}$$

$$E(A_V, c_V) = A_V \cdot c_V \cdot L \cdot \left[1 - \text{EXP}\left(a + \frac{b_1}{A_V \cdot c_V} + \frac{b_2}{A_V^2 \cdot c_V}\right)\right] \quad \text{(Equation B)}$$

$$Q_3(x(r, t)) = \frac{\int_{E_{min}}^{E(r)} \frac{r^2}{A_V(x(r, t))} dE(r)}{\int_{E_{min}}^{E_{max}} \frac{r^2}{A_V(x(r, t))} dE(r)} \quad \text{(Equation C)}$$

$$c_V(r, t) = c_{V,ges} \cdot Q_3(x(r, t)) = \quad \text{(Equation D)}$$
$$\frac{E(r, t)}{Q_3(r, t) \cdot \int_0^\infty [A_V(x(r, t)) \cdot q_3(x(r, t))] dx}$$

$$\mu(c_V(r, t)) = \frac{\mu_{app}(c_V(r, t))}{\mu_C} \quad \text{(Equation E*)}$$

-continued $$\Phi(c_V(r, t)) = \frac{c_V(r, t) \cdot (1 - c_V(r, t))^2}{\mu(c_V(r, t))} \quad \text{(Equation F)}$$

$$\eta(c_V(r, t)) = \frac{v}{v_{Stokes}} = \frac{(1 - c_V(r, t))^2}{\mu(c_V(r, t))} \quad \text{(Equation E)}$$

$$x(r, t) = \sqrt{\frac{18 \cdot \mu_C}{(\rho_P - \rho_F) \cdot \omega^2 \cdot t \cdot \eta(c_V(r, t))} \cdot \ln\left(\frac{r}{r_0}\right)} \quad \text{(Equation G)}$$

Exemplary Embodiment 2

Determination of the Distribution of Particle Sizes for Sediment Samples, Ascertainment of the Extinction Coefficients from the Course of the Extinction for a Sample of Known Distribution In the example, the distribution of particle sizes was determined on the basis of the segregation kinetics of 2 sediment samples (fraction <63 μm).

Reference measurement: The distribution of particle sizes was determined by means of a reference method (sedimentation in the normal gravitational field, detection by means of X-ray absorption, radiation attenuation proportional to the mass concentration). The ascertained distribution is to be gathered from Table 1.

TABLE 1

| | Results from the Sedigraph measurements (spherical shape assumption, particle density 2.65 g/cm³) | | | | | |
|---|---|---|---|---|---|---|
| Sample | m % < 2 μm | m % < 10 μm | m % < 16 μm | m % < 20 μm | m % < 50 μm | m % < 63 μm |
| A | 56.1 | 92.4 | 97.1 | 98.7 | 99.3 | 99.1 |
| B | 64.7 | 95.3 | 99.6 | 100.3 | 101.1 | 100.6 |

Preparation of samples: In the first step, the sediment samples were diluted to a concentration of approximately 1 m % by adding the dispersing agent sodium pyrophosphate (0.13 m %). These dispersions were then mixed with sugar for calibrating a favorable viscosity such that aqueous dispersions with approximately 0.5% solid substance is present in 50% sugar solution.

The sediment dispersions were treated for 15 minutes 3 times in an ultrasonic bath in order to achieve the most complete dispersion and degasification.

Experiment: The centrifugal analysis was performed with 12 samples at the same time (6 parallel determinations in each case) using plastic cuvettes with a film thickness of approximately 2.2 mm with a rotor speed of a constant 500 revolutions per minute. Sample A served as a reference sample, which means the known distribution for this sample was used for the determination of the dependency of the extinction coefficients on the particle size. This dependency was used in order to calculate the distribution of particle sizes for Sample B from the measurement results, and to compare them with the results of the reference measurement for Sample B.

The determination of cumulative distribution of particle sizes was performed on the basis of the ascertainment of the mass fraction for the particle fraction, which had already precipitated out of the sample completely at the different points in time at which the transmission was measured. The temporal course of the transmission averaged over the rotor position from 106.5 to 107.5 mm was used for the analysis. This position was 6 mm above the bottom of the cuvette.

The diameter of the particle x, which had all already passed rotor position 107 mm at the time of the measurement, was calculated on the basis of Equation H:

$$x^2 = \frac{18 \cdot \mu_C}{\Delta \rho \cdot \omega^2 \cdot t} \cdot \ln\left(\frac{r}{r_0}\right) \quad \text{(Equation H)}$$

with: $\Delta_\rho$ Difference in the density between dispersed substance and dispersion medium $\mu_C$ Viscosity of the dispersion medium $\omega$ Angular speed $R_0$ Radial position of the fill level $R_A$ Average radial position for the transmission analysis It was calculated with the values for $\mu_C$=15 mPa s, $\Delta\rho$=1.4 g/cm³ (same sample density that serves as the basis for the reference measurement).

A conversion of the measured transmission values T (%) into extinction values $E_T(t, R_A)$ is necessary for the data analysis. The experimentally determined transmission values for the samples are to be corrected advantageously according to Equation I with respect to the transmission of the cuvettes $T_{cell}$ (empty value) filled with the dispersion medium. One obtains the temporal change for the extinction in the range from 106.5 to 107.5.

$$E_T(t, R_A) = -\ln\left(\frac{T(t, R_A)}{T_{cell}(t, R_A)}\right) \quad \text{(Equation I)}$$

The changes to the extinction correspond to the change in the local particle concentration, which is caused by the particle fraction that precipitated out (Equation H).

The temporal course of the extinction $E_T(t, R_A)$ was used in order to calculate, by means of the extrapolation of the extinction starting value $E_T(0, R_A)$, which original concentration and size distribution the tested sample corresponds to.

In an initial approximation, the cumulative distribution of particle sizes (uncorrected values) can be estimated from the temporal course of the relative extinction change $E_{rel}=E_T(t, R_A)/E_T(0, R_A)$. $E_T(0, R_A)$ corresponds to the uppermost threshold value for the distribution at a diameter of 63 μm (cumulative—100% m/m) and a value for $E_{rel}$=1. $E_{rel}$ corresponds, in a rough approximation, to the cumulative mass fraction for the particles that are smaller than the particles that have already precipitated out completely (Equation H).

In this case, the information about the starting concentration is not necessary, but the dependency of the extinction coefficients on the particle size is neglected.

In the example provided, this dependency was calculated with a known distribution of sizes from the simultaneously determined course of the extinction for Sample A. The following steps were necessary for this purpose.

Figure 1:
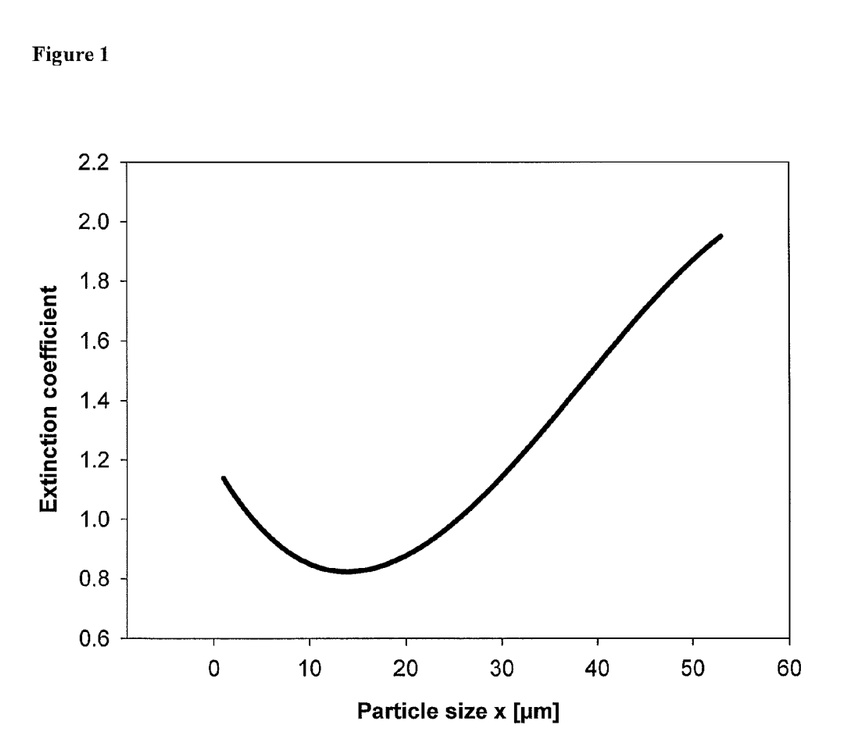
FIG. 1 is a graph showing the equalizing function for the extinction coefficients determined for Sample A, according to an exemplary aspect.

From the information on the cumulative distribution of particle sizes for Sample A for the mass fraction of particles smaller than 2, 10, 16, 20, 50 and 63 μm, a distribution function % m/m=f(d [μm]) was recalculated by means of the equalising function $$y = \frac{a}{\left(1 + \frac{x}{x_0^b}\right)}. \quad \text{(Equation J)}$$

Other equalizing functions can be used as well.

The range of particle sizes between 1.5 and 63 μm ascertained via the measurement was split into sub-fractions. The extinction coefficients were determined for these sub-fractions by comparing the changes in the mass fractions corresponding to Equation J with the change in the extinction ($E_T(t, R_A)$) in this range.

The equalizing function $$y = y_0 + a \cdot x + b \cdot x^2 + c \times x^3 \quad \text{(Equation K)}$$

with:

y—Extinction coefficient x—Particle diameter that was computed from this extinction coefficients is shown in FIG. 1 for Sample A.

This equalizing function was used with the ascertained parameters in order to determine the distribution of particle sizes for Sample B from the measurement data from the analytical centrifugation.

The range of the particle sizes was in turn split into sub-ranges for this purpose. Its concentration was calculated on the basis of Equation K from the relative change in the extinction and the respective extinction coefficients (corresponding to the average values for the particle diameter for the sub-range). The cumulative distribution of particle sizes then results from the mass concentration of the starting sample and the mass concentration of the sub-fractions.

Figure 2:
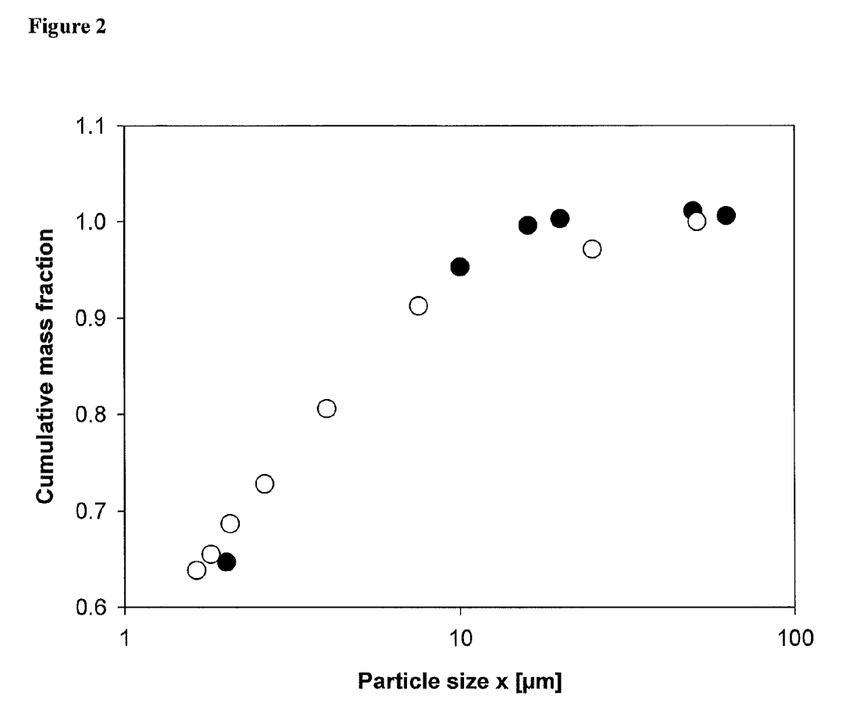
FIG. 2 is a graph which compares the results of the reference measurement with the experimentally determined values for Sample B, according to an exemplary aspect.

The distribution function determined in this manner for Sample B (empty symbols) shows very good agreement with the results from the reference measurement (filled symbols, see FIG. 2).

It can therefore be concluded that for samples that are similar to one another, a routine determination of the distribution of particle sizes is possible according to the described method without prior knowledge of the extinction coefficients.

Exemplary Embodiment 3

Determination of the Hindrance and Flux Density Function for a Monodisperse Silicon Dioxide Sample In this example, the hindrance function was determined on the basis of the segregation kinetics of a monodisperse silicon dioxide suspension with a particle size of 550 nm.

Preparation of samples: For the determination of the hindrance function and thus the measurement of a dilution sequence, a concentrated starting suspension of approximately 15% by volume was prepared and diluted to the desired concentrations (10, 5, 4, 3, 2, 1, 0.85, 0.65, 0.5, 0.4, 0.3, 0.2 and 0.1% by volume). The dispersion of the starting suspension was performed as follows.

First, the powder was stirred in deionized water with a magnetic stirrer. In a second step, the suspension was treated for 15 minutes in each case with a high-speed disperser based on the rotor/stator principle until the distribution of particle sizes (measurement with laser diffraction) no longer changed. Then the suspension was further dispersed with an ultrasonic dispersion apparatus in pulse mode. This process was likewise repeated until the distribution of particle sizes did not change. Finally, the pH value was adjusted to the value of 8 by adding 0.1 M KOH, and the solid substance concentration was measured with a thermal scale. The individual dilution stages were produced from the starting suspension with deionized water and treated in the ultrasonic bath for 5 minutes prior to the test in order to ensure complete dispersion and degasification.

Experiment: The centrifugal analysis was performed with 8 samples three times and 4 samples once at the same time (4 and 2 parallel determinations for controls in each case) using plastic cuvettes with a film thickness of approximately 2.2 mm with a rotor speed of a constant 2000 revolutions per minute.

The determination of the hindrance function was carried out on the basis of the ascertainment of the sink speeds v from the segregation kinetics, in which the position of the phase boundary between fluid free of solid substance and suspension was applied over the time for each dilution stage. The increase in the resulting segregation curve is the average measured sedimentation speed. This was then divided by the theoretical Stokes sink speed (Equation E and Equation L).

$$v_{Stokes} = \frac{(\rho_P - \rho_F) \cdot x \cdot r \cdot \omega^2}{18 \cdot \mu_c} \quad \text{(Equation L)}$$

with:

$\rho_p$ Density of the dispersed substance 2.0 g/cm³
$\rho_F$ Density of the dispersion medium 0.994 g/cm³
$\mu c$ Viscosity of the dispersion medium 0.722 mPa s
x Particle size
$\omega$ Angular speed 209 1/s
r Average position $((R_0+R_a)/2)$ So that the hindrance function is available for concentrations other than those tested experimentally, the concentration dependency for the measured sink speeds in terms of the Stokes was adjusted exemplarily to the following function (Equation M) with the least squares method.

$$\eta = \frac{v}{v_{Stokes}} = a \cdot c_V^3 + b \cdot c_V^2 + c \cdot c_V + d \quad \text{(Equation M)}$$

with:

$\eta$ Hindrance function
v Measured speed
$v_{Stokes}$ Sink speed according to Equation 5
$c_V$ Volume concentration
a, b, c, d Factors for the adjustment to the experimental data The following fit parameters were computed for the example above (stability index 0.9920):

a=−379 b=112 c=−13.21 d=1

Figure 3:
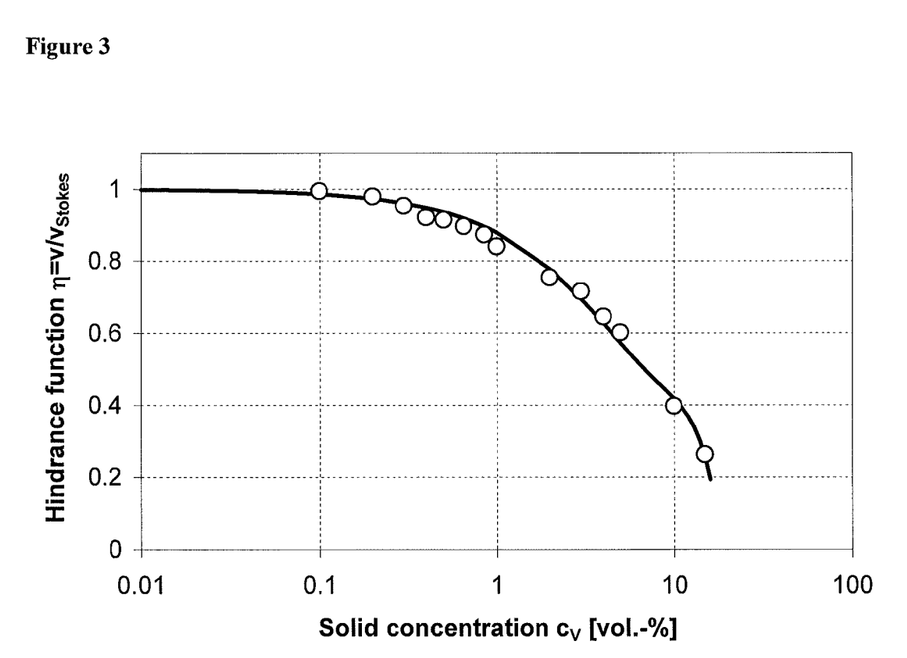
FIG. 3 is a graph which compares the experimental hindrance function (symbols) with the calculated hindrance function (line), according to an exemplary aspect.

FIG. 3 represents the hindrance function (measured values and adjustment equation) depending on the concentration of solid substance, and shows the good correlation of the experimental values (symbols) with the calculated values (line).

On the basis of the equation above, the hindrance function necessary for the calculation of the particle size for concentrated dispersions can be computed for any volume concentrations. In addition, the relative concentration-dependent viscosity $\mu(c_V)$ can be calculated by dividing $(1-c_V)^2$ by $\eta(c_V)$ (Equation M1).

$$\mu(c_V) = \frac{(1-c_V)^2}{\eta(c_V)} = \frac{(1-c_V)^2}{a \cdot c_V^3 + b \cdot c_V^2 + c \cdot c_V + d} \quad \text{(Equation M1)}$$

Using Equation M, the flux density function $\Phi(c_V)$ can also be calculated for any volume concentrations corresponding to Equation M2.

$$\Phi(c_V) = c_V \cdot \eta(c_V) = a \cdot c_V^4 + b \cdot c_V^3 + c \cdot c_V^2 + d \cdot c_V \quad \text{(Equation M2)}$$

Exemplary Embodiment 4

Determination of the Distribution of Particle Sizes of a Latex Sample Evaluated Based on Volume In this example, the distribution of particle sizes for a polydisperse latex sample was calculated from position-dependent extinction profiles at different times t and from the time-dependent extinction at different established position ranges (r+δr) for the cuvettes.

Preparation of samples: The original samples were stirred up and diluted with 1% sodium dodecyl sulfate to a solid substance concentration of 3.5% m/m latex, and then poured into the cuvettes made of polycarbonate (2.2 mm layer thickness). The net weight amounted to approximately 0.47 g.

Experiment: The centrifugal analysis was carried out with 2 samples at the same time (parallel determinations) at a rotor speed of a constant 4000 revolutions per minute (corresponding to 2300 times the acceleration of gravity). The temperature during the test amounted to a constant 25° C. The centrifugation time amounted to approximately 14 hours at a measurement reading interval of 150 seconds.

A conversion of the measured transmission values T(r, t) into extinction values E(r, t) was necessary for the data analysis. The experimentally determined transmission values for the samples are to be corrected for it corresponding to Equation N with respect to the transmission for the cuvettes filled only with the dispersion medium $T_0(r)$ (blank value, determined for the same cuvettes in a prior experiment or for a cuvette constructed in the same way in the same course).

$$E(r, t) = -\ln\left(\frac{T(r, t)}{T_0(r)}\right) \quad \text{(Equation N)}$$

On the one hand, the determination of the cumulative distribution of particle sizes takes place on the basis of the ascertainment of the mass fraction for the particle fraction, which has already completely precipitated out of the sample at various points in time at which the transmission was measured. As an example, the temporal courses of the extinctions averaged over the rotor positions first from 114.5 to 115.5 mm, second from 120.5 to 120.5 mm and third from 124.5 to 125.5 mm were used for the analysis. With the help of the Equations O through Q, the cumulative distribution of particle sizes $Q_3(x)$ was calculated at the positions 115 mm, 120 mm and 125 mm.

$$c_V = c_{V,0} \cdot \int_{x_{min}}^{x} \exp\left(\frac{-2 \cdot (\rho_P - \rho_F) \cdot \omega^2 \cdot t \cdot z^2}{18 \cdot \mu_C}\right) \cdot q_3(z) \, dz \quad \text{(Equation O)}$$

$$E = A_V \cdot c_V \cdot L \quad \text{(Equation P)}$$

$$dQ_3(x) = q_3(x) \cdot dx \quad \text{(Equation Q)}$$

with:

$Q_3(x)$ Cumulative distribution of particle sizes weighted by volume $q_3(x)$ Differential distribution of particle sizes weighted by volume $A_V(x)$ Volume-specific extinction cross section x Particle size E Extinction r Position t Time $c_v$ Volume concentration μc Viscosity of the dispersion medium 0.899 mPa s $\rho_P$ Density of the dispersed substance 1.23 g/cm³

$\rho_F$ Density of the dispersion medium 0.998 g/cm³

L Optical path length 2.2 mm

ω Angular speed 419 1/s

On the other hand, the radial dependency of the extinction at the times t=1023 s, t=1526 s, t=2029 s, t=2532 s and t=3035 s were used in order to calculate the cumulative distribution of particle sizes with the following equation R.

$$Q_3(x(r,t)) = \frac{\int_{E_{min}}^{E(r)} \frac{r^2}{A_V(x(r,t))} dE(r)}{\int_{E_{min}}^{E_{max}} \frac{r^2}{A_V(x(r,t))} dE(r)} \quad \text{(Equation R)}$$

with:

$Q_3(x)$ Cumulative distribution of particle sizes weighted by volume $A_V(x)$ Volume-specific extinction cross section x Particle size E Extinction r Position t Time The diameter of the particles x, which have already passed all of the rotor positions r at the time t, was calculated on the basis of Equation S.

$$x(r,t) = \sqrt{\frac{18 \cdot \mu_C}{(\rho_P - \rho_F) \cdot \omega^2 \cdot t} \cdot \ln\left(\frac{r}{r_0}\right)} \quad \text{(Equation S)}$$

with:

$\rho_P$ Density of the dispersed substance 1.23 g/cm³

$\rho_F$ Density of the dispersion medium 0.998 g/cm³

μc Viscosity of the dispersion medium 0.899 mPa s x Particle size

ω Angular speed 419 1/s r Position $r_0$ Position of the fill level t Time

Figure 4:
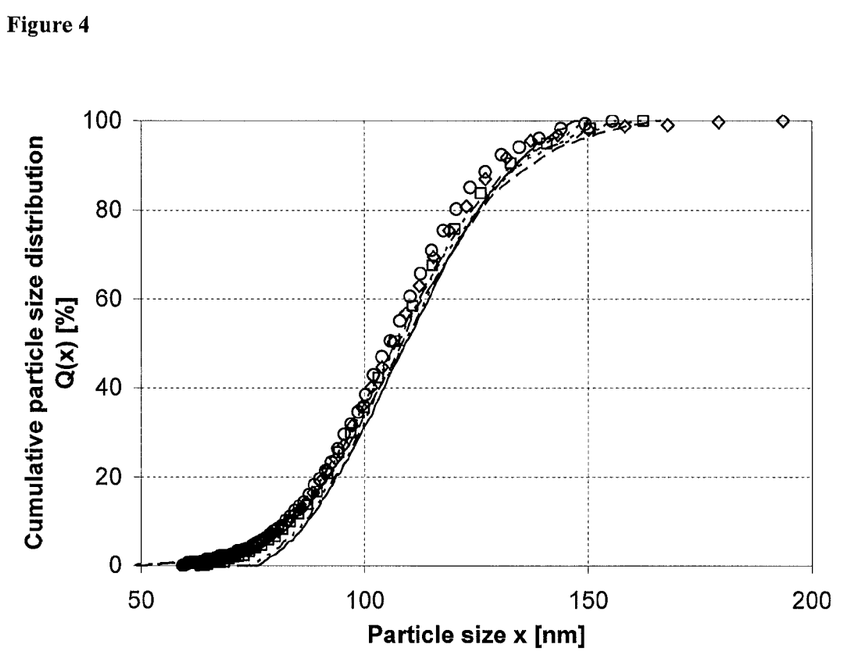
FIG. 4 is a graph showing the cumulative distributions of particle sizes Q(x) for the positions r=115 mm, 120 mm, 125 mm (symbols) and the times t=1023 s, 1526 s, 2029 s, 2535 s, 3035 s (lines), according to an exemplary aspect.

Ideally, all calculated distribution functions must fall one upon the other. The diagram in FIG. 4, in which the cumulative distributions of particle sizes Q(x) are plotted over the particle size x for the positions r=115 mm, 120 mm, 125 mm (symbols) and the times t=1023 s, 1526 s, 2029 s, 2535 s, 3035 s (lines), shows the very good correlation of all calculated distributions.

Exemplary Embodiment 5

Determination of the Particle Mass Density Distribution of a Pearl Cellulose Sample in the Gravitation Field In this example, the cumulative distribution of the particle density of a pearl cellulose sample characterized by an average porosity was determined from the segregation kinetics in the gravitation field. The particle diameter amounts to 40 μm.

Preparation of samples: The sample was placed in a beaker and then stirred for 10 minutes by means of a magnetic stirrer. Then the suspension was filled into the plastic cuvettes (2.2 mm film thickness) such that 99 mg of solid substance was obtained. The cuvette was then topped off to 504 mg of suspension with water, and shaken immediately prior to the start of the test in order to ensure that the sample is evenly stirred.

Experiment: The segregation analysis in the gravitation field was carried out at a temperature of 24.5° C. over a period of 255 times 14 seconds. At the same time, the transmission profiles were recorded in a range of 55 mm. The position of the fill level amounted to $h_0$=22.1 mm and the position of the bottom of the cuvette amounted to 48.8 mm.

A conversion of the measured transmission values T(h, t) into extinction values E(h, t) was necessary for the data analysis. The experimentally determined transmission values for the samples are to be corrected for it corresponding to Equation T with respect to the transmission for the cuvettes $T_{cell}$(h) filled only with the dispersion medium (blank value).

$$E(h,t) = -\ln\left(\frac{T(h,t)}{T_{cell}(h)}\right) \quad \text{(Equation T)}$$

The position-dependent course of the extinction at the time t E(r, t) was used in order to calculate the cumulative distribution of the particle density according to the following Equation U.

$$Q(\rho_P) = \frac{E(h,t)}{E_{max}(t)} \quad \text{(Equation U)}$$

with:

$Q(\rho_P)$ Cumulative distribution of the particle density

Figure 5:
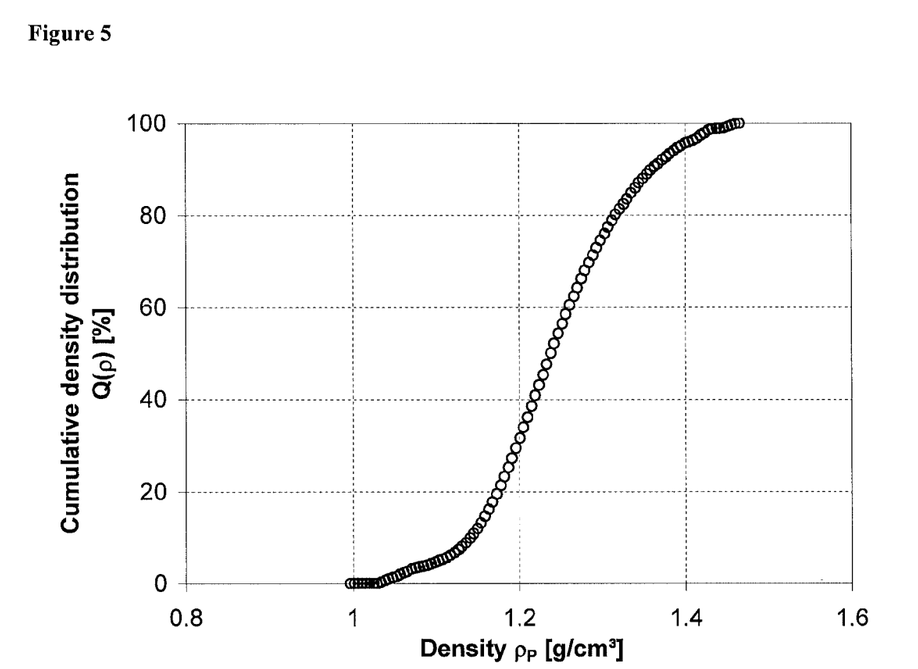
FIG. 5 is a graph showing the cumulative distribution of the particle density for the porous pearl cellulose determined from the transmission profile recorded at the time t=14 s, according to an exemplary aspect.
Figure 6:
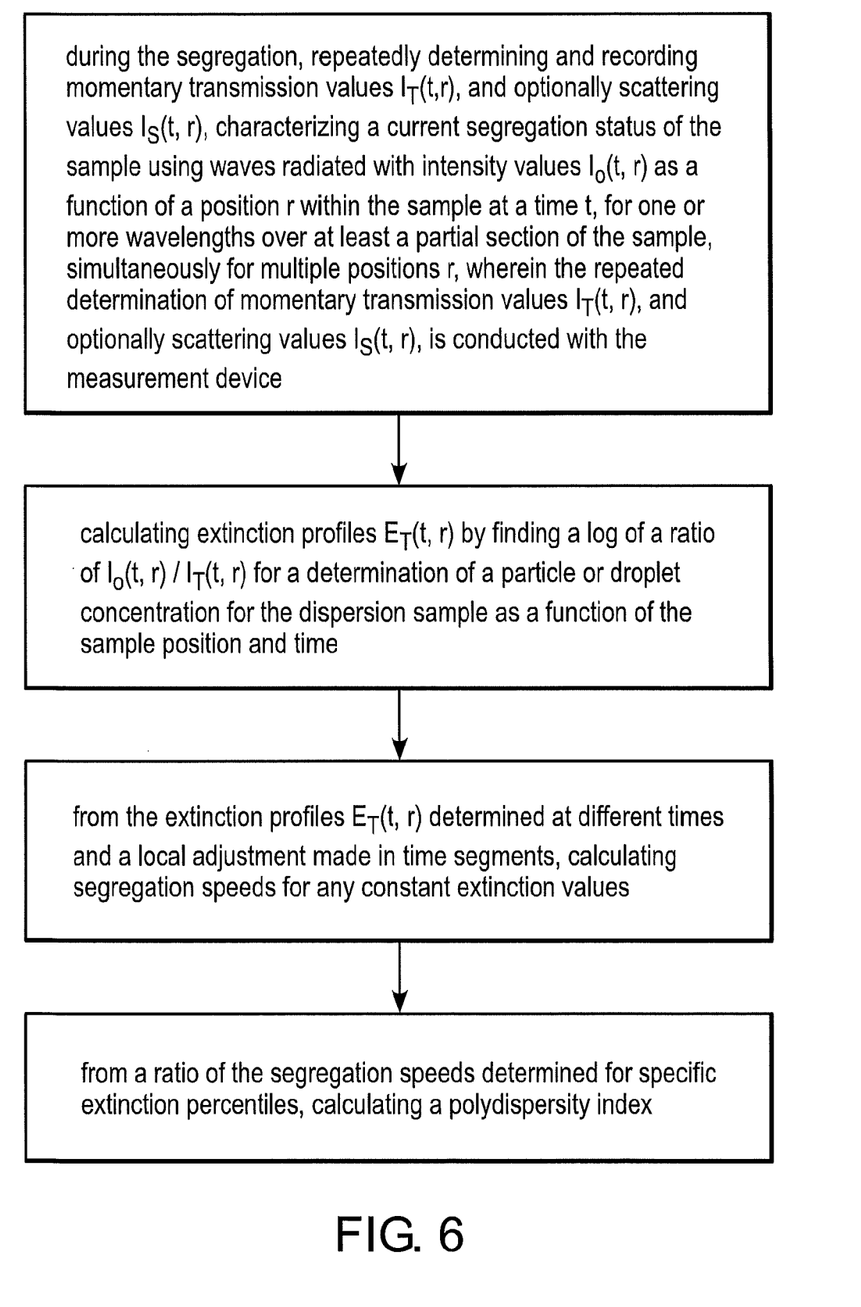
FIG. 6 is a diagram of a method for an automatic determination of a parameter of a sample using a measurement device, in accordance with an exemplary aspect.
Figure 7:
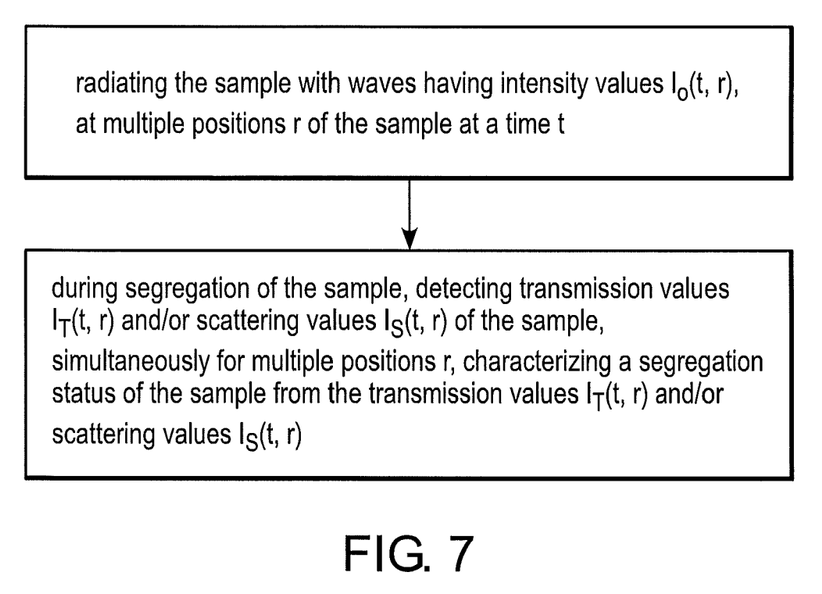
FIG. 7 is a diagram of a method for determining a parameter of a sample using a measurement device, in accordance with an exemplary aspect.
Figure 8:
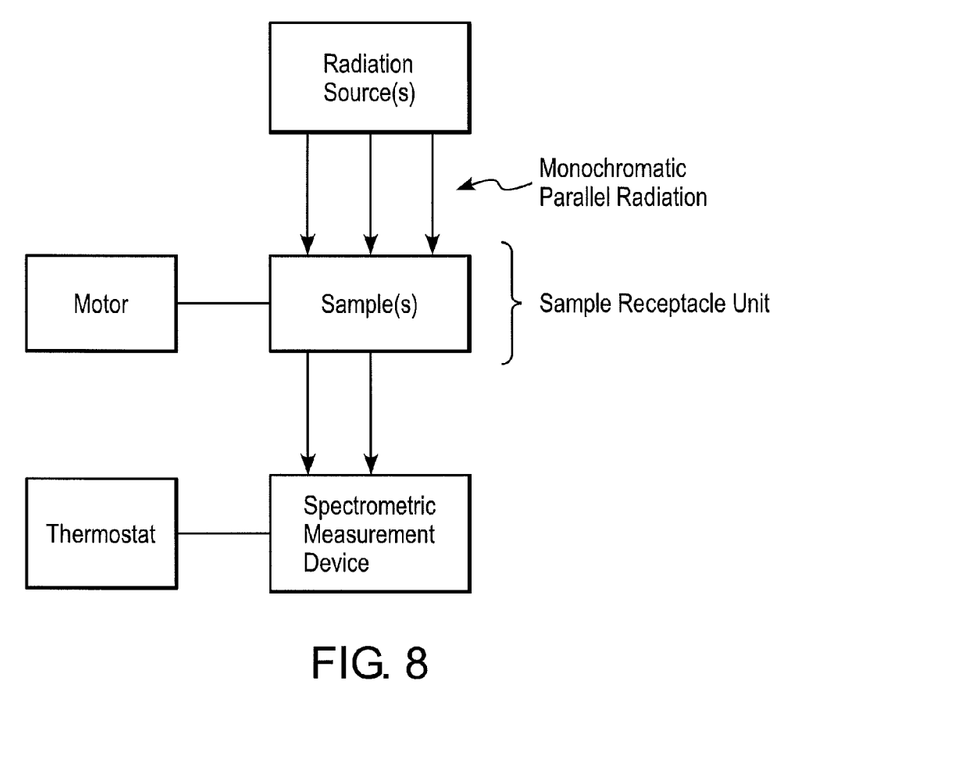
FIG. 8 depicts a device for an automatic determination of a parameter of a sample, in accordance with an exemplary aspect.

E(h,t) Extinction at the position h at time t $E_{max}(t)$ Maximum extinction at time t This approach is only valid as long as the extinction coefficient is not a function of the particle density. The substance system contemplated in this example fulfills this condition sufficiently The particle density $\rho_P$(h, t) of the particles, which have already passed the position h, was calculated on the basis of Equation V.

$$\rho_P(h,t) = \rho_F + \frac{18 \cdot (h - h_0) \cdot \mu_C}{g \cdot x^2 \cdot t} \quad \text{(Equation V)}$$

with:
$\rho_p$ Density of the dispersed substance
$\rho_F$ Density of the dispersion medium 0.997 g/cm$^3$
$\mu_c$ Viscosity of the dispersion medium 0.910 mPa s
x Particle size 4 µm
g Acceleration of gravity 9.81 m/s$^2$
h Position
$h_0$ Position of the fill level 22.1 mm
t Time 14 s FIG. 5 shows the calculated cumulative distribution of the particle density at the time t=14 s for the porous pearl cellulose. Cellulose generally has a solid substance density of 1.5 g/cm$^3$. This value naturally forms the upper limit of the density distribution, because the effective density results as an average of the solid substance density and of the water located in the pores.

The invention claimed is:

1. A device for an automatic determination of a parameter of a sample, the device comprising:
    a centrifuge including a rotor for receiving a dispersion sample;
    a source producing monochromatic parallel radiation, wherein the source is arranged to direct monochromatic parallel radiation to the sample; and
    a spectrometric measurement device which measures radiation intensity scattered or transmitted by the sample over a partial or entire length of the sample, simultaneously for multiple positions of the sample, and provides a radiation intensity measurement for each of the multiple positions at which a measurement is taken, wherein the radiation intensity measurements characterize a segregation status of the sample.

2. The device according to claim 1, wherein the sample receptacle unit comprises different cuvettes matched to a measurement task and/or the dispersion sample with respect to an optical path length, the cuvette type is detected automatically, and the parameters required for the analysis of the measurement results are automatically made available via database entries for a calculation of the parameter to be analyzed.

3. The device according to claim 1, wherein the source producing monochromatic parallel radiation comprises a plurality of radiation sources of different monochromatic wavelengths, whose radiation intensity $I_o(t, r)$ can be varied.

4. The device according to claim 1, further comprising a thermostat for controlling a measurement range and carrying out measurements at selectable temperatures both under as well as over room temperature.

5. The device according to claim 1, wherein the rotor is a multi-sample receptacle unit, and is driven by a motor with programmable variable and/or constant revolutions.

6. The device according to claim 5, wherein the multi-sample receptacle unit is capable of accepting samples placed vertically for segregation in a gravitational field.

7. A method for determining a parameter of a sample using a measurement device, the method comprising:
    radiating the sample with monochromatic parallel radiation waves having intensity values $I_o(t, r)$, at multiple positions r of the sample at a time t, wherein the waves are emitted from a spectrometric measurement device;
    during segregation of the sample, detecting transmission values $I_T(t, r)$ and/or scattering values $I_S(t, r)$ of the sample, simultaneously for multiple positions r, characterizing a concentration profile of the sample from the intensity values $I_o(t, r)$ and the transmission values $I_T(t, r)$ and/or scattering values $I_S(t, r)$.

8. The method according to claim 7, further comprising recording the transmission values $I_T(t, r)$ and/or scattering values $I_S(t, r)$.

9. The method according to claim 7, wherein the radiating, detecting and characterizing steps are repeatedly conducted.

10. The method according to claim 7, wherein the step of detecting transmission values $I_T(t, r)$ and/or scattering values $I_S(t, r)$, is conducted over substantially the entire length of the sample.

11. The method according to claim 7, wherein the step of detecting transmission values $I_T(t, r)$ and/or scattering values $I_S(t, r)$, is conducted for multiple samples.

12. The method according to claim 7, wherein at least transmission values $I_T(t, r)$ are detected, wherein the method further comprises calculating an extinction profile $E_T(t, r)$ of the sample as a function of the sample position r and time t, by finding a log of a ratio of $I_o(t, r)/I_T(t, r)$.

13. The method according to claim 7, wherein at least transmission values $I_T(t, r)$ are detected, wherein the characterizing step comprises calculating an extinction profile $E_T(t, r)$ by finding a log of a ratio of $I_o(t, r)/I_T(t, r)$ for a determination of a particle or droplet concentration for the sample as a function of the sample position and time.

14. The method according to claim 13, comprising calculating multiple extinction profiles $E_T(t, r)$ determined at different times, and from the extinction profiles $E_T(t, r)$, calculating segregation speeds.

15. The method according to claim 14, further comprising calculating a polydispersity index from a ratio of the segregation speeds determined for specific extinction percentiles.

16. The method according to claim 7, wherein the segregation of the sample is conducted by centrifugation.

17. The device according to claim 1, wherein the rotor is capable of being accelerated to between 600 and 24,000 revolutions per minute.

18. The method according to claim 16, wherein the dispersion sample is received on a rotor, and wherein the rotor is accelerated to between 600 and 24,000 revolutions per minute.

* * * * *